United States Patent

Hoehn

[11] 4,159,380
[45] Jun. 26, 1979

[54] IMIDAZOLYLETHOXY DERIVATIVES OF PYRAZOLO[3,4-B]PYRIDINE-5-METHANOLS

[75] Inventor: Hans Hoehn, Tegernheim, Fed. Rep. of Germany

[73] Assignee: E. R. Squibb & Sons, Inc., Princeton, N.J.

[21] Appl. No.: 923,418

[22] Filed: Jul. 10, 1978

[51] Int. Cl.$^2$ .................................. C07D 471//04
[52] U.S. Cl. .................................. 546/119; 424/256; 548/341
[58] Field of Search .............................. 546/119

[56] References Cited

U.S. PATENT DOCUMENTS

| 3,658,813 | 4/1972 | Godefroi et al. | 424/273 R |
| 3,717,655 | 2/1973 | Godefroi et al. | 424/273 R |
| 3,983,128 | 9/1976 | Hoehn et al. | 546/119 |
| 3,991,201 | 11/1976 | Heeres et al. | 424/273 R |

OTHER PUBLICATIONS

Heeres et al., J. Med. Chem. 1976, vol. 19(9), pp. 1148–1155.
Godefroi et al., J. Med. Chem. 1969, vol. 12, pp. 784–791.
Heeres et al., J. Med. Chem. 1977, vol. 20(11), pp. 1511–1520.

Primary Examiner—John M. Ford
Assistant Examiner—Natalia Harkaway
Attorney, Agent, or Firm—Lawrence S. Levinson

[57] ABSTRACT

Imidazolylethoxy derivatives of pyrazolo-[3,4-b]pyridine-5-methanols having the general formula

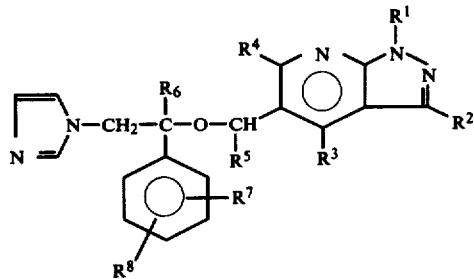

and their acid addition salts are useful as antifungal and antibacterial agents.

15 Claims, No Drawings

IMIDAZOLYLETHOXY DERIVATIVES OF PYRAZOLO[3,4-B]PYRIDINE-5-METHANOLS

SUMMARY OF THE INVENTION

This invention relates to new 2-(1H-imidazol-1-yl)ethoxy derivatives of pyrazolo[3,4-b]-pyridine-5-methanols and the acid addition salts of these compounds. These new compounds have the formula

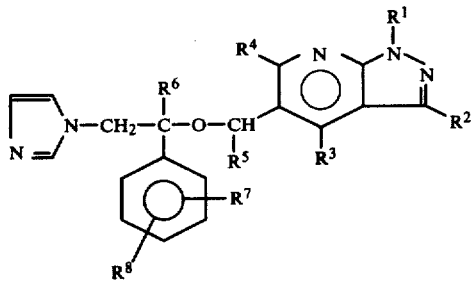

The symbols have the following meaning in formula I and throughout the specification:

$R^1$ is hydrogen, lower alkyl, phenyl, phenyl-lower alkyl, or cyclo-lower alkyl.

$R^2$, $R^4$, $R^5$ and $R^6$ each is hydrogen, lower alkyl, or phenyl.

$R^3$ is hydrogen, hydroxy, lower alkoxy, lower alkylthio, phenoxy, phenyl-lower alkoxy, halogen, or a basic nitrogen group

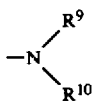

wherein $R^9$ and $R^{10}$ each is hydrogen, lower alkyl, phenyl or substituted phenyl wherein the phenyl substituent is halogen, hydroxy, lower alkoxy, lower alkyl, mercapto, lower alkylthio, cyano or nitro.

$R^7$ and $R^8$ are hydrogen, halogen, hydroxy, lower alkylthio, lower alkyl or nitro.

DETAILED DESCRIPTION OF THE INVENTION

The lower alkyl groups include straight or branched chain hydrocarbon groups containing 1 to 7 carbon atoms. Examples of the type of groups contemplated are methyl, ethyl, propyl, isopropyl, etc. The lower alkoxy and lower alkylthio groups include such lower alkyl groups bonded to an oxygen or sulfur, respectively, e.g., methoxy, ethoxy, propoxy, butoxy, t-butoxy, methylthio, ethylthio, propropylthio, butylthio, isobutylthio, etc. The phenyl-lower alkyl groups are similar having a phenyl ring attached to lower alkyl groups of the type described. In all of these the $C_1$–$C_4$, especially $C_1$–$C_2$, lower alkyl groups are preferred.

The cyclo-lower alkyl groups refer to the 3 to 7 carbon atom alicyclic groups, cyclopropyl, cyclobutyl, cyclopentyl, cyclohexyl and cycloheptyl. The 5 and 6-membered rings are preferred.

The halogens are the four common halogens, chlorine and bromine being preferred in that order. Preferably all halogens in a single compound are the same.

The substituted phenyl groups refer to phenyl rings bearing one of the simple substituents named.

The basic nitrogen groups

include for example amino; lower alkylamino, e.g., methylamino, ethylamino, propylamino and the like; di(lower alkyl)amine, e.g., dimethylamino, diethylamino, methylethylamino, dipropylamino, dibutylamino and the like; phenylamino; diphenylamino; 2-, 3- or 4-chlorophenylamino; 2-, 3- or 4-bromophenylamino; hydroxyphenylamino; (lower alkoxyphenyl)amino, e.g. 2-, 3- or 4-methoxyphenylamino; (lower alkylphenyl)amino, e.g., 2-, 3- or 4-methylphenylamino; mercaptophenylamino; (lower alkyl mercaptophenyl)-amino, e.g., methylthiophenylamino; cyanophenylamino or nitrophenylamino.

Preferred embodiments of this invention are compounds of formula I wherein $R^1$ is hydrogen, lower alkyl of 1 to 4 carbons, phenyl, benzyl, phenethyl or cycloalkyl of 5 or 6 carbons.

$R^2$, $R^4$ and $R^6$ each is hydrogen, lower alkyl of 1 to 4 carbons or phenyl.

$R^3$ is hydrogen, hydroxy, lower alkoxy of 1 to 4 carbons, phenoxy, halogen or the basic nitrogen group

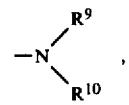

with $R^9$ and $R^{10}$ independently selected from hydrogen, lower alkyl of 1 to 4 carbons, phenyl, hydroxyphenyl, halophenyl or lower alkylphenyl, only one of $R^9$ or $R^{10}$ preferably being phenyl or substituted phenyl.

$R^7$ and $R^8$ each is hydrogen, lower alkyl of 1 to 4 carbons, or halogen (preferably chlorine or bromine).

The most preferred embodiments are compounds of formula I wherein $R^1$ is hydrogen or lower alkyl of 1 to 4 carbons, especially hydrogen or ethyl.

$R^2$ is hydrogen or lower alkyl of 1 to 4 carbons, especially hydrogen or methyl.

$R^3$ is hydrogen, lower alkoxy of 1 to 4 carbons or halogen, especially hydrogen, ethoxy or chlorine.

$R^4$, $R^5$ and $R^6$ each is hydrogen, lower alkyl of 1 to 4 carbons, or phenyl, especially hydrogen, ethyl, butyl, or phenyl, and most especially hydrogen. Preferably one of $R^4$, $R^5$ and $R^6$ is other than hydrogen.

$R^7$ and $R^8$ each is hydrogen or halogen especially hydrogen or chlorine.

The new compounds of formula I are formed by the following series of reactions.

A pyrazolo[3,4-b]-pyridine-5-methanol of the formula

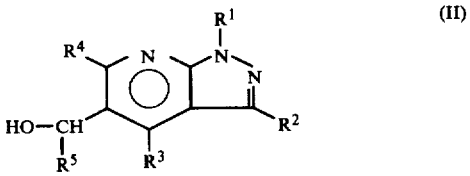

is converted to the halo product of the formula

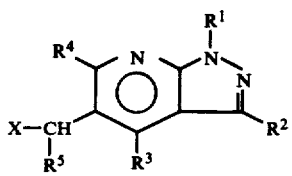

wherein X represents chlorine, bromine or iodine, by means of an inorganic acid halide such as thionyl chloride, phosphorus oxybromide, etc.

The product of formula I is then prepared by reaction of the halo compound of formula III with a substituted 1-(phenyl)-2-(1H-imidazol-1-yl)-ethanol of the formula

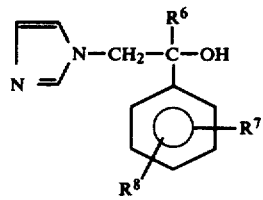

The inorganic acid formed during the reaction is neutralized by a base, e.g., alkali metal hydroxide, carbonate, amine, alcoholate or other suitable means known in the art.

The compounds of formula II which are used as starting materials are described in U.S. Pat. No. 3,983,128, issued Sept. 28, 1976, and can be produced as described in that patent.

The reactants of formula IV are prepared by the general method described in J. Med. Chem. 12, 784 (1969).

The compounds of formula I form salts which are also part of this invention. The salts include acid-addition salts, particularly the non-toxic, physiologically acceptable members. The bases of formula I form salts by reaction with one or more equivalents of any of a variety of the common inorganic and organic acids providing acid addition salts including, for example, hydrohalides (especially hydrochloride and hydrobromide), sulfate, nitrate, borate, phosphate, oxalate, tartrate, maleate, citrate, acetate, ascorbate, succinate, benzenesulfonate, methanesulfonate, cyclohexanesulfamate and toluenesulfonate. The acid addition salts frequently provide a convenient means for isolating or purifying the product, e.g., by forming and precipitating a salt (which is not necessarily non-toxic) in an appropriate medium in which the salt is insoluble, then after separation of the salt, neutralizing with a base such as barium hydroxide or sodium hydroxide, to obtain the free base of formula I. Other salts may then be formed from the free base by reaction with one or more equivalents of acid containing the desired acid group.

The new compounds of Formula I and their salts are useful as anti-fungal agents and may be used to combat infections in various mammalian species, such as mice, rats, dogs, guinea pigs and the like, particularly those due to organisms such as Candida albicans, as well as organisms such as Trichomonas vaginalis or Trichophyton mentagrophytes. For example, a compound or mixture of compounds of formula I or physiologically acceptable acid addition salt thereof can be administered orally to an infected animal, e.g., to a mouse, in an amount of about 5 to 25 mg. per kg. per day in 2 to 4 divided doses. These may be conventionally formulated in a tablet, capsule or elixir containing about 10 to 250 mg. per dosage unit, by compounding the active substance or substances with the conventional excipient, vehicle, binder, preservative, flavor, etc., as called for by accepted pharmaceutical practice. Preferably they are applied topically, e.g., intravaginally in a lotion or in a conventional cream base at a concentration of about 0.01 to 3 percent by weight for a period of about 3 to 7 days, two to four times daily.

The following examples are illustrative of the invention. Temperatures are on the celsius scale.

EXAMPLE 1

4-Chloro-5-[[1-(2,4-dichlorophenyl)-2-(1H-imidazol-1-yl)ethoxy]methyl]-1-ethyl-3-methyl-1H-pyrazolo-[3,4-b]pyridine, hydrochloride (a) 4-Chloro-5-chloromethyl-1-ethyl-3-methyl-1H-pyrazolo[3,4-b]pyridine Into a three necked flask, fitted with a stirrer, reflux condenser and dropping funnel are added 94.6 g. of 4-chloro-1-ethyl-3-methyl-1H-pyrazolo[3,4-b]pyridine-5-methanol (0.42 mol.) (U.S. Pat. No. 3,983,128; Example 2). While stirring 475 ml. of thionyl chloride are added dropwise within 45 minutes and the mixture is then refluxed for one and a half hours. The excess thionyl chloride is removed by a rotary evaporator and the residue is dissolved in benzene. The solvent is again removed and the remaining solid product is triturated with ligroin, filtered and dried at 70°, yield 91 g. of 4-chloro-5-chloromethyl-1-ethyl-3-methyl-1H-pyrazolo[3,4-b]pyridine, which, after recrystallization from hexane, gives 83.5 g. of pure product, m.p. 96°-97°. Evaporation of the ligroin mother liquor and recrystallization of the residue gives a second crop of 5.7 g. (m.p. 95°-96°). Total yield: 89.2 g. (87%).

(b) 4-Chloro-5-[[1-(2,4-dichlorophenyl)-2-(1H-imidazol-1-yl)ethoxy]methyl]-1-ethyl-3-methyl-1H-pyrazolo[3,4-b]pyridine, hydrochloride (1:1)

In a three necked flask (250 ml.), fitted with a stirrer, reflux condenser and gas inlet tube are introduced 24.4 g. of sodium hydroxide (0.61 mol.) and 23 ml. of water. While passing nitrogen through the flask, the solution is cooled to 45° and then are added 6.43 g. of 1-(2,4-dichlorophenyl)-2-(1H-imidazol-1-yl)ethanol (0.025 mol.), [prepared according to J. Med. Chem., Vol. 12, 784 (1969)], 0.43 g. of benzyltrimethylammonium chloride and 25 ml. of tetrahydrofuran. To the mixture, which is warmed to 50°, a solution of 6.1 g. of 4-chloro-5-chloromethyl-1-ethyl-3-methyl-1H-pyrazolo[3,4-b]-pyridine (0.025 mol.) in 10 ml. of tetrahydrofuran is added from a prewarmed dropping funnel within 3 minutes. The mixture is stirred vigorously for 3 hours at 60° using a water bath. Then the warm mixture is transferred into a separating funnel, the lower aqueous sodium hydroxide is extracted with 10 ml. of tetrahydrofuran. The combined tetrahydrofuran layers are dried by means of sodium sulfate and after the solvent has been removed the residual oil is extracted with ether, treated with charcoal and filtered. To the solution of free base are added dropwise 5.9 ml. of ethereal hydrochloric acid (30.9%). The precipitated 4-chloro-5[[1-(2,4-dichlorophenyl)-2-(1H-imidazol-1-yl)ethoxy]methyl]-1-ethyl-3-methyl-1H-pyrazolo[3,4-b]pyridine, hydrochloride is filtered off, dried in the vacuum desiccator and recrystallized from acetonitrile, m.p. 200°–201°; yield 5.67 g. (45%).

EXAMPLE 2

4-Chloro-5-[[1-(4-chlorophenyl)-2-(1H-imidazol-1-yl)ethoxy]methyl]-1-ethyl-3-methyl-1H-pyrazolo[3,4-b]pyridine, hydrochloride The procedure of Example 1b is followed but 5.6 g. (0.025 mol.) of 1-(4-chlorophenyl)-2-(1H-imidazol-1-yl)ethanol is substituted for the 1-(2,4-dichlorophenyl)-2-(1H-imidazol-1-yl)-ethanol. In contrast to Example 1b the final product crystallizes. After cooling to room temperature, the slurry is sucked off in a sintered glass funnel. Then the solid is suspended in 50 ml. of water, neutralized with acetic acid, again filtered, washed with water, and dried at 70°. Recrystallization from acetonitrile yields 5.6 g. (52%) of pure product, m.p. 176°–177°.

To 5.4 g. of this product, 4-chloro-5-[[1-(4-chlorophenyl)-2-(1H-imidazol-1-yl)ethoxy]methyl]-1-ethyl-3-methyl-1H-pyrazolo[3,4-b]pyridine dissolved in 15 ml. of absolute alcohol and 5 ml. of alcoholic hydrochloric acid (184 g. HCl/l) by slight warming, are added 120 ml. of ether. The precipitated hydrochloride is filtered off after standing overnight, washed with a mixture of ether and alcohol (5:1) and dried, yield 6.3 g. (100%); m.p. 184°–185°.

EXAMPLE 3

4-Chloro-5-[[1-(2,4-dichlorophenyl)-2-(1H-imidazol)-1-yl)ethoxy]methyl]-1-ethyl-1H-pyrazolo[3,4-b]pyridine, hydrochloride (a) 4-chloro-5-chloromethyl-1-ethyl-1H-pyrazolo]3,4-b]pyridine 150 ml. of thionyl chloride are added carefully to 20 g. of 4-chloro-1-ethyl-1H-pyrazolo[3,4-b]-pyridine-5-methanol (0.094 mol.) (U.S. Pat. No. 3,983,128; Example 1) so that warming and gas evolvement take place gently. The mixture is allowed to stand overnight and after that time excess thionyl chloride is distilled off by the rotary evaporator and the residue is treated with ice. The crystalline 4-chloro-5-chloromethyl-1-ethyl-1H-pyrazolo[3,4-b]pyridine is sucked off, washed with water and dried in a vacuum desiccator over phosphorus pentoxide, yield: 19.7 g. (91%), on recrystallization from hexane, m.p. 73°–74°.

(b) 4-chloro-5-[[1-(2,4-dichlorophenyl)-2-(1H-imidazol-1-yl)ethoxy]methyl]-1-ethyl-1H-pyrazolo[3,4-b]pyridine, hydrochloride 7.71 g. of 1-(2,4-dichlorophenyl)-2-(1H-imidazol-1-yl)-ethanol (0.03 mol.) and 6.9 g. of 4-chloro-5-chloromethyl-1-ethyl-1H-pyrazolo[3,4-b]pyridine (0.03 mol.) are reacted according to the procedure of Example 1b. The combined tetrahydrofuran layers are treated with charcoal and filtered. Addition of 250 ml. of ether to the tetrahydrofuran solution separates an oily impurity which is removed by decanting the solution. After the solution containing the free base is cleared up by the addition of Hyflo filter aid there is added an excess of ethereal hydrochloric acid. The precipitated hydrochloride is allowed to stand for 2 hours, then filtered off, washed with ether and dried in a vacuum desiccator, yield: 8.3 g. (61%). The product is recrystallized from 3 N-hydrochloric acid with charcoal. The so obtained 4-chloro-5-[[1-(2,4-dichlorophenyl)-2-(1H-imidazol-1-yl)ethoxy]methyl]-1-ethyl-1H-pyrazolo[3,4-b]-pyridine, hydrochloride (1:1) contains half a mole of water; m.p. 166°–167°.

EXAMPLE 4

5-[[1-(2,4-Dichlorophenyl)-2-(1H-imidazol-1-yl)ethoxy]methyl]-1-ethyl-3-methyl-1H-pyrazolo[3,4-b]-pyridine, hydrochloride (a) 1-ethyl-3-methyl-1H-pyrazolo[3,4-b]pyridine-5-carboxylic acid, ethyl ester To 80.3 g. of 4-chloro-1-ethyl-3-methyl-1H-pyrazolo[3,4-b]pyridine-5-carboxylic acid, ethyl ester (0.3 mol.) [prepared according to Journal of Heterocyclic Chemistry 9, 235–253 (1972)] dissolved in 270 ml. glacial acetic acid, are added 33.4 g. of triethylamine (0.33 mol.) and 7.5 g. of palladium on charcoal (10%). The mixture is hydrogenated at room temperature and a pressure of 2.5 atm. After about 19 hours the theoretical amount of hydrogen is absorbed. Then the catalyst is filtered off and the filtrate evaporated. The residue is treated with 200 ml. of water and extracted with ether. The combined ether extracts are dried and the ether distilled off. The oily 1-ethyl-3-methyl-1H-pyrazolo[3,4-b]pyridine-5-carboxylic acid, ethyl ester is distilled in vacuo; b.p.$_{0.3}$ 144°–146°, which after a short time begins to crystallize, yield: 64.5 g. (92%).

(b) 1-Ethyl-3-methyl-1H-pyrazolo[3,4-b]pyridine-5-methanol, hydrochloride 49 g. of 1-Ethyl-3-methyl-1H-pyrazolo[3,4-b]-pyridine-5-carboxylic acid, ethyl ester (0.21 mol.) are dissolved in 250 ml. of anhydrous tetrahydrofuran. Nitrogen is passed through the flask and, while stirring and cooling with tap water, 6 g. of lithium aluminum hydride (0.16 mol.) are added in small portions keeping the reaction temperature at 20°. Stirring is continued for an additional three hours at room temperature. Then 3 N-hydrochloric acid (380 ml.) is added, while cooling the flask with ice water, and the cloudy solution is evaporated in vacuo. The residue is dissolved in 95 ml. of hot water and the solution is allowed to stand over the week-end. The crystallized product (8 g. m.p. 207°–208°) is discarded. The aqueous mother liquor is extracted with three 100 ml. portions of chloroform. The combined chloroform extracts are dried with sodium sulfate and evaporated in vacuo. The resulting oily-crystalline mass is sucked off, washed with acetonitrile and dried at 70°, yield: 10 g. (21%) of 1-ethyl-3-methyl-1H-pyrazolo-[3,4-b]pyridine-5-methanol, hydrochloride (1:1); m.p. 169°–170°. A sample recrystallized from acetonitrile melts at 170°–171°.

(c) 5-Chloromethyl-1-ethyl-3-methyl-1H-pyrazolo[3,4-b]-pyridine, hydrochloride (1:1)

To 11 g. of 1-ethyl-3-methyl-1H-pyrazolo-[3,4-b]pyridine-5-methanol (0.057 mol.), dissolved in 50 ml. of anhydrous benzene are added dropwise 55 ml. of thionyl chloride. A white suspension formed by this reaction is stirred for an additional three hours at room temperature. Then the slurry is sucked off, washed with benzene and dried at 70°, yield: 6.6 g. of 5-chloromethyl-1-ethyl-3-methyl-1H-pyrazolo[3,4-b]pyridine, hydrochloride (1:1); m.p. 154°–157°.

Evaporation of the mother liquor, dissolving the residue in chloroform and removing the solvent yield an additional crop of 7.4 g. (m.p. 152°–154°), total yield: 14 g. (100%).

(d) 5-[[1-(2,4-Dichlorophenyl)-2H-(1H-imidazol-1-yl)ethoxy]methyl]-1-ethyl-3-methyl-1H-pyrazolo-[3,4-b]pyridine, hydrochloride 7.71 g. of 1-(2,4-dichlorophenyl)-2-(1H-imidazol-1-yl)-ethanol (0.03 mol.) and 7.4 g. of 5-chloromethyl-1-ethyl-3-methyl-1H-pyrazolo[3,4-b]-pyridine, hydrochloride (0.03 mol.) are reacted according to the procedure of Example 1b. The combined tetrahydrofuran layers are treated with charcoal, filtered and dried with sodium sulfate. After addition of 300 ml. of ether and filtering over charcoal, the filtrate containing the free base is mixed with 8 ml. of ethereal hydrochloric acid (415 g. HCl/1) (0.09 mol.). The precipitated 5-[[1-(2,4-dichlorophenyl)-2H-(1H-imidazol-1-yl)-ethoxy]methyl]-1-ethyl-3-methyl-1H-pyrazolo[3,4-b]-pyridine, hydrochloride (14.8 g.) is treated with ether, filtered off, dried in the vacuum desiccator and recrystallized from acetone; m.p. 158°–159° (dec.); yield: 8.11 g. (58%).

The following additional products of formula C are obtained by the procedure of Example 1b by reacting the unsubstituted or substituted 2-(1H-imidazol-1-yl)-ethanol of formula A with the unsubstituted or substituted 5-chloromethyl-1H-pyrazolo[3,4-b]pyridine of formula B. The substituents apply to the respective formulas.

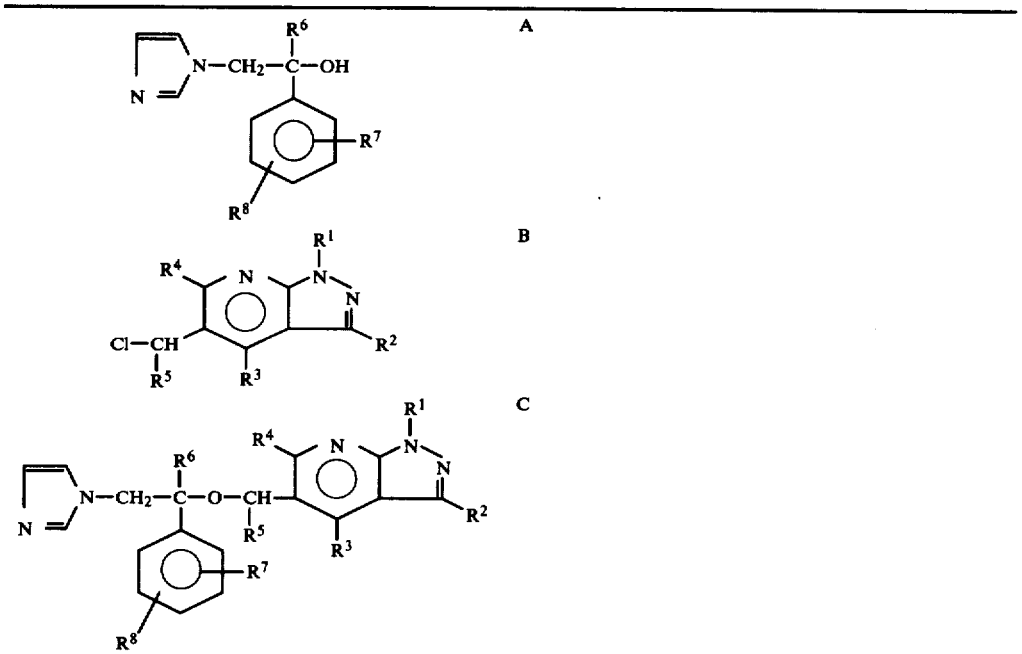

| Example | $R^1$ | $R^2$ | $R^3$ | $R^4$ | $R^5$ | $R^6$ | $R^7$ | $R^8$ |
|---|---|---|---|---|---|---|---|---|
| 5 | H | H | H | H | H | H | H | H |
| 6 | $CH_3$ | $CH_3$ | —OH | $C_6H_5$ | H | H | H | H |
| 7 | $C_2H_5$ | H | —$OC_2H_5$ | —$CH_3$ | H | H | 2—Cl | 4-Cl |
| 8 | $C_2H_5$ | $C_2H_5$ | —$OCH_3$ | $CH_3$ | H | H | H | 4-Cl |
| 9 | $C_2H_5$ | $CH_3$ | Br | H | H | H | H | 3-Br |
| 10 | $C_2H_5$ | $CH_3$ | H | H | H | H | 2-Br | 4-Br |
| 11 | $C_2H_5$ | H | Br | H | H | H | 3-Br | 4-Br |
| 12 | $C_2H_5$ | H | H | $CH_3$ | —$C_6H_5$ | H | H | 4-Cl |
| 13 | $C_2H_5$ | H | Cl | $C_2H_5$ | H | H | H | 2-Cl |
| 14 | $C_2H_5$ | $CH_3$ | —$OC_2H_5$ | H | H | —$CH_3$ | 2-$CH_3$ | 4-$CH_3$ |
| 15 | $C_2H_5$ | $C_3H_7$ | Cl | H | H | H | H | 4-$OCH_3$ |
| 16 | $C_2H_5$ | H | Cl | $C_6H_5$ | H | H | H | 2-$OCH_3$ |
| 17 | $C_3H_7$ | H | —OH | H | H | H | H | 3-Cl |
| 18 | $C_6H_5$ | H | Cl | H | H | H | 2-Cl | 4-Cl |
| 19 | $C_6H_4CH_2$— | $CH_3$ | H | H | H | H | H | 4-Cl |
| 20 | $C_6H_4CH_2CH_2$— | H | Cl | H | H | H | H | H |
| 21 | ⟨S⟩ | H | Cl | H | H | H | 2-Cl | 4-Cl |
| 22 | ⟨S⟩ | $CH_3$ | Cl | H | H | H | 3-Cl | 4-Cl |
| 23 | $C_2H_5$ | $C_6H_5$ | Cl | H | H | H | H | 4-Cl |
| 24 | $C_2H_5$ | $CH_3$ | H | H | H | $C_6H_5$ | 2-Cl | 4-Cl |
| 25 | $C_2H_5$ | $CH_3$ | Cl | H | $C_2H_5$ | H | H | 4-Cl |
| 26 | H | $CH_3$ | —$NHC_4H_9$ | H | H | H | H | 4-Cl |
| 27 | $C_2H_5$ | $CH_3$ | —$NHCH_3$ | H | H | H | H | H |
| 28 | $C_2H_5$ | H | —$NH_2$ | H | H | H | 2-Cl | 4-Cl |
| 29 | $C_2H_5$ | H | —$N(C_2H_5)_2$ | $CH_3$ | H | H | H | 4-Br |

-continued
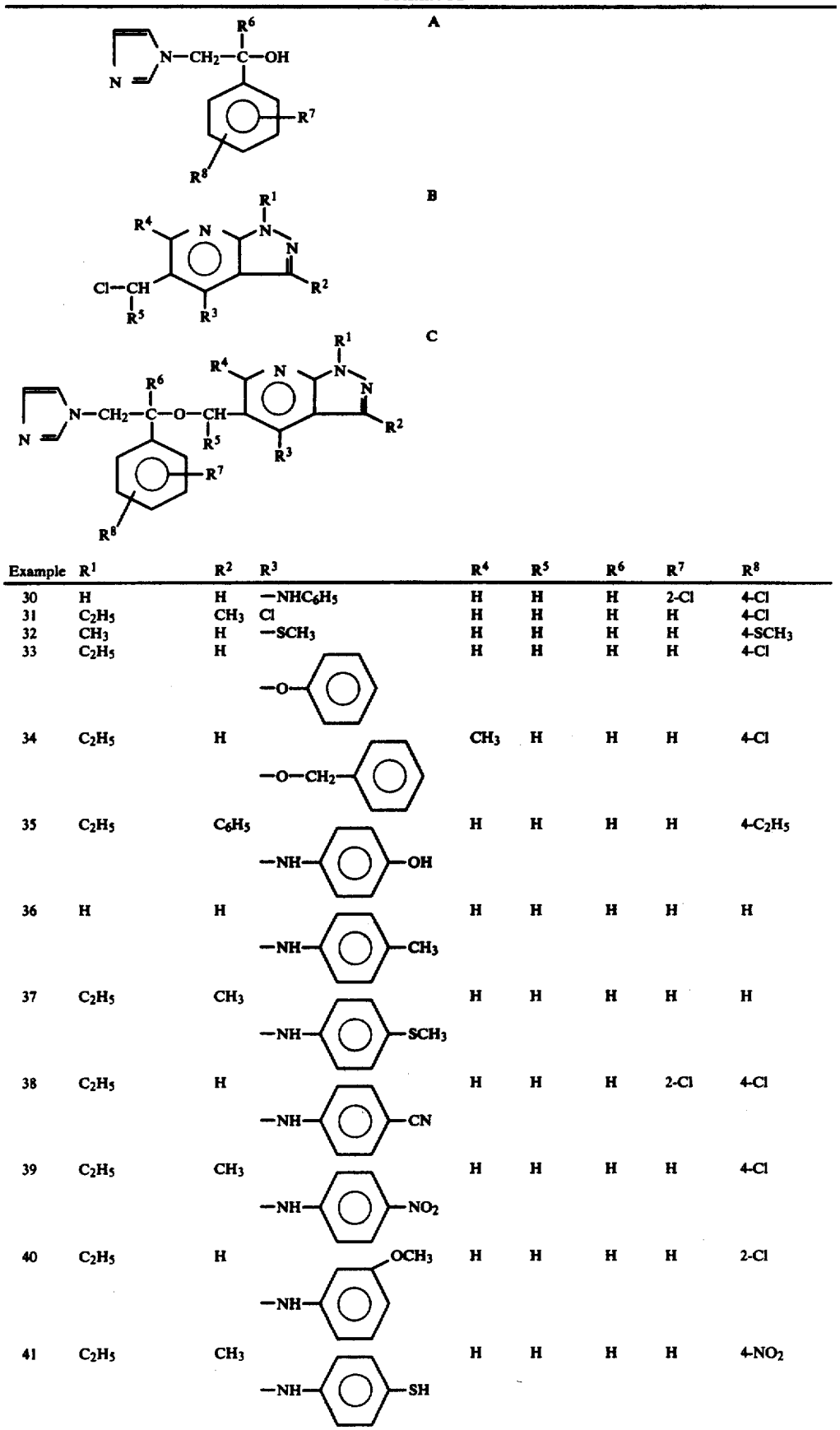
| Example | R¹ | R² | R³ | R⁴ | R⁵ | R⁶ | R⁷ | R⁸ |
|---|---|---|---|---|---|---|---|---|
| 30 | H | H | —NHC₆H₅ | H | H | H | 2-Cl | 4-Cl |
| 31 | C₂H₅ | CH₃ | Cl | H | H | H | H | 4-Cl |
| 32 | CH₃ | H | —SCH₃ | H | H | H | H | 4-SCH₃ |
| 33 | C₂H₅ | H | —O—⟨phenyl⟩ | H | H | H | H | 4-Cl |
| 34 | C₂H₅ | H | —O—CH₂—⟨phenyl⟩ | CH₃ | H | H | H | 4-Cl |
| 35 | C₂H₅ | C₆H₅ | —NH—⟨phenyl⟩—OH | H | H | H | H | 4-C₂H₅ |
| 36 | H | H | —NH—⟨phenyl⟩—CH₃ | H | H | H | H | H |
| 37 | C₂H₅ | CH₃ | —NH—⟨phenyl⟩—SCH₃ | H | H | H | H | H |
| 38 | C₂H₅ | H | —NH—⟨phenyl⟩—CN | H | H | H | 2-Cl | 4-Cl |
| 39 | C₂H₅ | CH₃ | —NH—⟨phenyl⟩—NO₂ | H | H | H | H | 4-Cl |
| 40 | C₂H₅ | H | —NH—⟨phenyl-OCH₃⟩ | H | H | H | H | 2-Cl |
| 41 | C₂H₅ | CH₃ | —NH—⟨phenyl⟩—SH | H | H | H | H | 4-NO₂ |

-continued

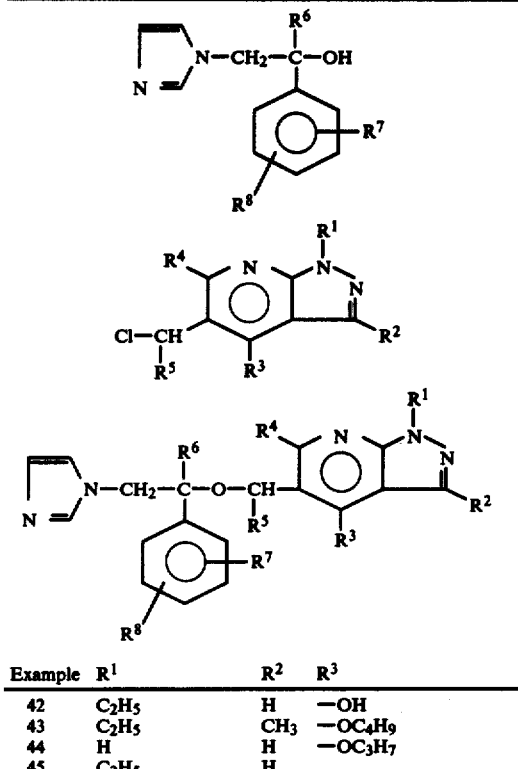

| Example | R¹ | R² | R³ | R⁴ | R⁵ | R⁶ | R⁷ | R⁸ |
|---------|-----|-----|-----|-----|-----|-----|-----|-----|
| 42 | C₂H₅ | H | —OH | H | H | H | 3-OH | 5-OH |
| 43 | C₂H₅ | CH₃ | —OC₄H₉ | H | H | H | H | 4-Cl |
| 44 | H | H | —OC₃H₇ | H | H | H | 2-Cl | 4-Cl |
| 45 | C₂H₅ | H | —OCH₂—C₆H₅ | H | H | H | 2-Cl | 4-Cl |
| 46 | C₂H₅ | H | Cl | CH₃ | CH₃ | C₆H₅ | H | 4-Cl |

What is claimed is:

1. A compound of the formula

wherein
$R^1$ is hydrogen, lower alkyl, phenyl, phenyl-lower alkyl or cyclo-lower alkyl;
$R^2$, $R^4$, $R^5$ and $R^6$ each is hydrogen, lower alkyl or phenyl;
$R^3$ is hydrogen, hydroxy, lower alkoxy, lower alkylthio, phenoxy, phenyl-lower alkoxy, halogen or

wherein $R^9$ and $R^{10}$ each is hydrogen, lower alkyl, phenyl or substituted phenyl wherein the phenyl substituent is halogen, hydroxy, lower alkoxy, lower alkyl, mercapto, lower alkylthio, cyano or nitro;
$R^7$ and $R^8$ each is hydrogen, halogen, hydroxy, lower alkoxy, lower alkylthio, lower alkyl or nitro; and physiologically acceptable acid addition salts thereof.

2. A compound as in claim 1 wherein $R^3$ is choro.
3. A compound as in claim 1 wherein $R^5$ is hydrogen.
4. A compound as in claim 1 wherein $R^1$ and $R^2$ each is lower alkyl.
5. A compound as in claim 1 wherein $R^1$ is hydrogen, lower alkyl of 1 to 4 carbons, phenyl, benzyl, phenethyl or cycloalkyl of 5 or 6 carbons; $R^2$, $R^4$, $R^5$ and $R^6$ each is hydrogen, lower alkyl of 1 to 4 carbons or phenyl; $R^3$ is hydrogen, hydroxy, lower alkoxy of 1 to 4 carbons, phenoxy, benzyloxy, halogen or

wherein $R^9$ and $R^{10}$ each is hydrogen, lower alkyl of 1 to 4 carbons, phenyl, hydroxyphenyl, halophenyl or lower alkylphenyl; $R^7$ and $R^8$ each is hydrogen, lower alkyl of 1 to 4 carbons or halogen; and physiologically acceptable acid addition salts thereof.

6. A compound as in claim 1 wherein $R^1$ and $R^2$ each is hydrogen or lower alkyl of 1 to 4 carbons; $R^3$ is hydrogen, lower alkoxy of 1 to 4 carbons or halogen; $R^4$, $R^5$ and $R^6$ each is hydrogen, lower alkyl of 1 to 4 carbons or phenyl; and $R^7$ and $R^8$ each is hydrogen or halogen; and physiologically acceptable acid addition salts thereof.

7. A compound as in claim 1 wherein $R^1$ and $R^2$ each is lower alkyl; $R^3$, $R^7$ and $R^8$ each is halogen; and $R^4$, $R^5$ and $R^6$ each is hydrogen.

8. A compound as in claim 1 wherein $R^1$ and $R^2$ each is lower alkyl; $R^3$, $R^4$, $R^5$ and $R^6$ each is hydrogen; and $R^7$ and $R^8$ each is halogen.

9. A compound as in claim 1 wherein $R^1$ is lower alkyl; $R^2$, $R^4$, $R^5$ and $R^6$ each is hydrogen; and $R^3$, $R^7$ and $R^8$ each is halogen.

10. A compound as in claim 1 wherein $R^1$ and $R^2$ each is lower alkyl; $R^2$ and $R^8$ each is halogen; and $R^4$, $R^5$, $R^6$ and $R^7$ each is hydrogen.

11. The compound as in claim 1 wherein $R^1$ is ethyl; $R^2$ is methyl; $R^3$ is chloro; $R^4$, $R^5$ and $R^6$ each is hydrogen; $R^7$ is 2-chloro; $R^8$ is 4-chloro; and physiologically acceptable acid addition salts thereof.

12. The hydrochloride of the compound of claim 11.

13. The compound as in claim 1 wherein $R^1$ is ethyl; $R^2$ is methyl; $R^3$, $R^4$, $R^5$ and $R^6$ each is hydrogen; $R^7$ is 2-chloro; and $R^8$ is 4-chloro.

14. The compound as in claim 1 wherein $R^1$ is ethyl; $R^2$, $R^4$, $R^5$ and $R^6$ each is hydrogen; $R^3$ is chloro; $R^7$ is 2-chloro; and $R^8$ is 4-chloro.

15. The compound as in claim 1 wherein $R^1$ is ethyl; $R^2$ is methyl; $R^3$ is chloro; $R^4$, $R^5$, $R^6$ and $R^7$ each is hydrogen; and $R^8$ is 4-chloro.

* * * * *